United States Patent [19]

Madhavan et al.

[11] 4,192,795
[45] Mar. 11, 1980

[54] BARIUM ALUMINUM SILICATE FILLER FOR U.V. CURABLE COMPOSITES

[75] Inventors: Narayanan Madhavan, Dearborn Heights; Frank H. Freeman, Farmington, both of Mich.

[73] Assignee: Sybron Corporation, Rochester, N.Y.

[21] Appl. No.: 837,787

[22] Filed: Sep. 29, 1977

[51] Int. Cl.² ............................................. C08K 3/40
[52] U.S. Cl. ............................. 260/42.52; 260/42.15; 260/998.11
[58] Field of Search ............. 260/42.15, 42.52, 998.11, 260/DIG. 36; 204/159.16

[56] References Cited

U.S. PATENT DOCUMENTS

| | | | |
|---|---|---|---|
| 3,539,533 | 11/1970 | Lee et al. | 260/42.52 |
| 3,766,132 | 10/1973 | Lee et al. | 260/42.52 |
| 3,801,324 | 4/1974 | Dietz | 32/15 |
| 3,826,778 | 7/1974 | Dietz | 32/15 |
| 3,911,581 | 10/1975 | Dietz | 260/42.52 |
| 3,973,972 | 8/1976 | Muller | 260/42.53 |
| 3,974,104 | 8/1976 | Foster et al. | 252/478 |
| 3,975,203 | 8/1976 | Dietz | 106/299 |

*Primary Examiner*—Lewis T. Jacobs
*Attorney, Agent, or Firm*—Theodore B. Roessel; Owen D. Marjama

[57] ABSTRACT

A single paste photopolymerizable dental restoration composition which utilizes a barium-aluminum-silicate glass filler material.

2 Claims, No Drawings

BARIUM ALUMINUM SILICATE FILLER FOR U.V. CURABLE COMPOSITES

BACKGROUND OF THE INVENTION

Many dental restorative products are designed as two part systems. Specific quantities of the two parts, for example, two pastes, are mixed together to initiate a chemical reaction which will result in the mixture solidifying or setting to a hard rigid state, to cause the product to serve its intended purpose. The properties of the final product depend to a large extent upon how well and how fast one performs the mixing. Failure to produce a homogeneous mix may create irregularities within the restoration.

The advent of low volatility, shelf stable, single paste restorative products, which are activated by actinic radiation permit the manufacture of a product which overcomes the above noted disadvantages associated with two part systems. In the single paste photopolymerizable system, it is a continuing objective to match materials which achieve a rapid cure rate which result in high strength restorations.

It is therefore an object of this invention to provide an improved dental process and product which exhibits advantages over the above noted two paste products.

It is another object of the present invention to provide a new composition and process for forming UV initiated dental restorative materials which exhibit accelerated cure rates over conventional single paste materials.

SUMMARY OF THE INVENTION

It has been discovered that the curing of photopolymerizable dental restoration composites are dramatically affected by the composition of the filler material. The use of barium-aluminum-silicate glass has shown a very unique and unexpected accelerating affect on the cure rate of resin based composites. In the U.V. spectrum range at about 3600 Å, solid quartz is known to have exceptional U.V. translucency, but particulate quartz does not induce the cure rates found with the particulate barium-aluminum-silicate glass of the present invention. The unique application of the filler material of the present invention in U.V. initiated systems results in a dental restoration composite which cures more rapidly to a greater depth and which exhibits higher strengths than conventional composites.

DETAILED DESCRIPTION OF THE INVENTION

Photopolymerizable compounds suitable for use in the present invention comprise a monomer resin containing unsaturated sites which are capable of undergoing polymerization, a diluent monomer to control the viscosity of the resin, a filler or a combination of fillers, an accelerator which increases the speed of photo reaction of the composition, and an initiator which produces free radicals on exposure to actinic radiation, which then react with the double bond of the monomer to initiate polymerization. The resin used in the preparation of this single paste may be derived from the reaction of glycidyl ether of bisphenol A with methacrylic acid or acrylic acid:

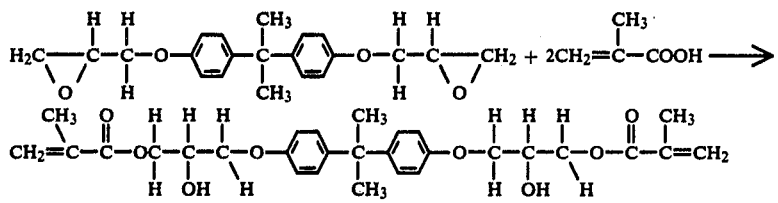

This glycidyl methacrylate derivative of bisphenol-A is known as bisphenol A-bis(3 methacrylato-2-hydroxypropyl)ether. The resin serves as a binder for the photopolymerizable dental composition, and is hereinafter referred to as Bis-GMA. Modification of this resin can also be used or any other resin having polymerizable ethylenic likages will work.

The diluent monomer used may be selected from alkyl methacrylates, alkylene dimethacrylates, trimethacrylates, alkyl acrylates, alkylene diacrylates, and triacrylates. Some of the suitable monomers are represented by:

Triethyleneglycoldimethacrylate
1,6-hexanedioldiacrylate
1,3-butylenedimethacrylate One or more of these monomers can be used. The diluent monomers copolymerize with Bis-GMA resin on exposure to actinic radiation in the presence of a photoinitiator and accelerator. The accelerator increases the speed of the reaction.

Another component present in the composite is a polymerization inhibitor which prevents the premature polymerization of the Bis-GMA resin and diluent monomer and is present only in small quantities. The suitable polymerization inhibitors are hydroquinons (HQ), methyl ether of hydroquinone (MEHQ) and butylated hydroxytoluene (BHT).

The initiators used in this invention are alpha diketones and their derivatives having the following general formula:

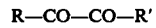

Where R and R' can be same or different aliphatic or aromatic groups and their derivatives. These photo initiators are slightly yellow in color. Since they are present in small quantities, the final polymerized product is almost colorless.

Photo accelerators are chemical compounds which in the presence of initiators accelerates the photoreaction. The accelerators help polymerization penetrate a restoration placed into deep cavity preparation. The accelerators are amines (primary, secondary and tertiary) and diamines. Some examples are dimethylparatoluidines, N,N'-dimethylbenzylamine, N-methyldibutylamine, triethylamine, trihexylamine, etc. Examples of diamine, N,N,N',N-tetra ethyl ethylenediamine and N,N,N',N'-tetramethyl 1,6-hexanediamine.

In the absence of the previously mentioned photo initiators, these amines do not function to induce photopolymerization. Even though all amines in combination with the previously mentioned photoinitiators accelerate to some extent, the tertiary amines (e.g., triethylamine, trihexyl amine, etc.) are found to be the best for causing polymerization deep into the composite mass. Amines with aromatic groups are not desirable as they impart a slight color on prolonged exposure to light.

The photopolymerizable dental restorative product may have from about 50 to 85% by weight refractory filler. According to the present invention, the filler comprises a barium-aluminum-silicate glass. A suitable range of concentration comprises by weight 25–40% $SiO_2$; 35–55% BaO; and 15–30% $Al_2O_3$. As will be more fully discussed later, the use of barium-aluminum-silicate glass exhibits a unique and unexpected accelerating affect on the cure rate of the resin based composites. This results in a dental restoration composite which is easy and quick to cure and which exhibits higher strengths than conventional composites.

The particle size distribution of the filler varies from less than 5 to approximately 40 microns. The filler is preferably silanated in order to increase the bonding between the inorganic filler and the organic matrix material. The silane bonding agents have a general formula $RSiX_3$, $R_2SiX_2$ and $R_3SiX$, where X may be halogen, alkoxy or hydroxy group and R may be vinyl, methacrylate, allyl, methallyl itaconate, maleate, acrylate, itaconate, maleate acrylate aconitrate, fumarate, alkyl, aryl, alkenyl crotonate, cinnamate and citraconate, sorbate or glycidyl groups. When silanation is complete a mono molecular coating of the bonding agent is present on the filler surface, which improves the adhesion between the filler and the resin matrix.

The following formulation was found to be satisfactory:

|  | Parts by Weight |
|---|---|
| BisGMA (including MEHQ 200 ppm) | 10–20 |
| Diluent Monomer (including HQ 100 ppm) | 2–5 |
| Benzil (purity 99.5%) | .001–1 |
| Trihexylamine | .01–1 |
| Barium Aluminum Silicate Filler | 70–85 |

The fillers examined during the development of the present invention comprise boro-barium-aluminum-silicate, lithium-aluminum-silicate, barium-aluminum-silicate, and fused quartz. The compositions of these fillers, except for the fused quartz which is 100% $SiO_2$, are shown in Table I below:

TABLE I

| | Composition of Glass Fillers | | | | | |
|---|---|---|---|---|---|---|
| | Lithium Aluminum Silicate | | Boro-Barium Aluminum Silicate | | Barium- Aluminum Silicate | |
| | Mol % | Wt % | Mol % | Wt % | Mol % | Wt % |
| $SiO_2$ | 51 | 51.3 | 67 | 51.2 | 51 | 32.2 |
| BaO | 0 | 0 | 16.5 | 31.8 | 28.3 | 45.6 |
| $B_2O_3$ | 0 | 0 | 10 | 8.7 | 0 | 0 |
| $Al_2O_3$ | 20.1 | 34.3 | 6.5 | 8.3 | 20.7 | 22.2 |
| $Li_2O$ | 28.9 | 14.4 | 0 | 0 | 0 | 0 |

A general method of preparing UV initiated composites suitable for use in the present invention is as follows:

All these fillers are powdered until the particle size distribution of the fillers varies from about 5 to 40 microns. These fillers are preferrably first silanated in order to increase the bonding between the inorganic filler and organic material. The bonding agent used is silane A-174 (γ methacryloxy propyl trimethoxysilane). The filler is treated with 50% of its weight of acetone, and 1% of A-174. The mixture is rolled in a ball mill for complete dispersion for an hour. The mixture is poured in a try like vessel and allowed to settle and the excess acetone decanted. The filler cake was dried in an oven at 280° F.–300° F. for one hour at temperature, ball milled one half hour, and sieved through a 160 mesh nitex cloth.

When silanation is complete, a mono molecular coating of the bonding agent is formed on the filler surface.

The composites are made with 4.2 grams of BisGMA resin

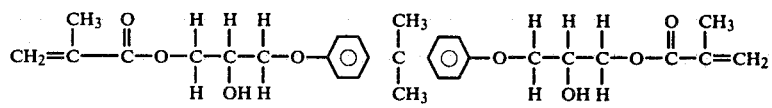

0.7 grams 1,6 hexane diacrylate $CH_2=CH_2COO(CH_2)_6OOCCH_2=CH_2$ 0.02 grams of benzil ($C_6H_5CO\ CO\ C_6H_5$)
0.05 grams of trihexylamine $N(CH_2CH_2CH_2CH_2CH_2CH_3)_3$ The resin is mixed with the diluent monomer, photo initiator and the accelerator. These are mixed well in a glass vessel by means of a Teflon (Reg. TM of duPont) rod. When the mix is fairly uniform, 24 grams of barium-aluminum-silicate filler is added and mixed well. Separate samples are also made using 16 grams of boro-barium-aluminum-silicate; 19.1 grams of lithium-aluminum-silicate; and 18.1 grams of fused quartz, respectively. The variance in weight of the fillers allows for their difference in density in order to insure that the volume of filler will be essentially the same in each sample. The well mixed heavy paste is packed in a split cylindrical polytetrafluoroethylene mold, 12.5 mm high by 6 mm diameter and open at both ends. The top and bottom were covered with Mylar (Reg. TM of duPont Co) strips and pressed to get a smooth surface. The Mylar covered ends were exposed for 15 seconds each to the light emitted from Spectroline B-100 high pressure mercury lamp at a distance of 4 inches. The range of emission for this lamp is from about 3000 to 4500 Å. The split mold was then opened and each side of the specimen exposed to actinic radiation for 15 seconds. The total exposure time is one minute. After 10 minutes post curing period, the strength of the material is measured in an Instron Universal Tester at a cross head speed of 0.02 inches per minute.

The crushing strengths varied according to the following order:

| Barium- Aluminum Silicate (32,000 psi) | Boro-Barium- Aluminum Silicate (25,500 psi) | Lithium- Aluminum Silicate (25,000 psi) | Fused Quartz (6,800 psi) |
|---|---|---|---|

Unpowdered quartz by itself has a high transmission of UV radiation. However, due to the difference in refractive index (UV region) or other factors, the powdered quartz is not a preferred filler in this resin system. The barium-aluminum-silicate on the other hand, appears to have unique advantages as a filler in the UV initiated system in that it renders the resin system easy and quick to cure thereby resulting in a high strength upon irradiation by UV light.

This unique filler is particularly useful in filling materials used in dentistry where deep cavities are to be restored quickly and completely.

The following examples further specifically define the present invention with respect to the method of making a single paste product. The parts and percentages in the disclosure are by weight unless otherwise indicated. The examples below are intended to illustrate various preferred embodiments of this invention.

EXAMPLE 1

A bulk solution is made by the general method outlined above and consists of 21 gms of BisGMA resin, 3.5 gms of 1,6 hexane diacrylate, 0.003 gms of benzil and 2 drops of trihexylamine. Four gms of this solution is separately treated with 2 gms of untreated lithium-aluminum-silicate, 2 gms of untreated boro-barium-aluminum-silicate glass, 2 gms of untreated fused quartz and 2.7 gms untreated barium-aluminum-silicate. Because of its high density, barium-aluminum-silicate is used at a higher by weight percent to give equal volume loading for comparison with that of lithium-aluminum-silicate.

The mixture is stirred and kept in an oven at 120° F. for 30 minutes to remove the air. A few drops of this solution is pressed against two glass slides so that a continuous film is formed between the plates. The film is then cured by exposure to a spectroline B-100 lamp for 15 minutes at a distance of 4 inches from the lamp. The film was scraped off carefully and the transmission measured between 400 nm and 300 nm; the UV region of the spectrum, in a Beckman DB-G double beam grating spectrometer. The measurements are made with air as reference and the resin film without filler as reference. The results are tabulated in Tables II and III. The high transmission of film in which barium-aluminum-silicate was incorporated explains the higher strengths of barium-aluminum-silicate incorporated composite material.

TABLE II

Transmission Characteristics of Different Fillers
Reference is Resin Mixture Film Having .11 mm Thickness

| Material and Resin Mixture | Thickness | % Transmission at Different Wave Lengths in Nanometers | | | | |
|---|---|---|---|---|---|---|
| | | 300 | 325 | 350 | 375 | 400 |
| Lithium Aluminum Silicate | 0.15 ± 0.03 mm | 1 | 1 | 1.5 | 3 | 4 |
| Quartz | | 0 | 0 | 0 | 0 | 0 |
| Boro-barium Aluminum Silicate | | 10 | 2 | 4 | 9 | 13.5 |
| Barium-Aluminum Silicate | | 22 | 92* | 72 | 45 | 34 |

*Maximum 95% transmission at 330 nm

TABLE III

Transmission Characteristics of Different Fillers.
Reference Air

| Material and Resin Mixture | Thickness mm | % Transmission at Different Wave Lengths in nanometers | | | | |
|---|---|---|---|---|---|---|
| | | 300 | 325 | 350 | 375 | 400 |
| Lithium-Aluminum-Silicate | 0.15 ± 0.03 | 0 | .5 | 1.0 | 2.0 | 3.0 |
| Quartz | | 0 | 0 | 0 | 0 | 0 |
| Borobarium-aluminum-silicate | | 3.5 | 4 | 5 | 7 | 10 |
| Barium-Aluminum-Silicate | | 0 | 49* | 47 | 34 | 27 |

*Maxiumum 52% transmission at 335 nm.

The dental restorative materials are made in different shades ranging from Light, Light Grey, Yellow, Universal, Dark Yellow, etc. The colored composites are made by incorporating different pigments, ususally the oxides of metals. As the pigment concentrations are increased, the penetration of ultraviolet will be reduced. This loss in strength can be compensated by incorporating more barium-aluminum-silicate in the composite.

EXAMPLE II

A composite is made and cured by the general method described above, using fused quartz as filler material. This composite exhibited a compressive strength of 6,840 pounds per square inch (psi) on one minute exposure. When approximately 20% of the quartz is replaced by barium-aluminum-silicate, the strength increased to 22,000 psi. When barium-aluminum-silicate is used alone, the strength increased to 32,000 psi.

The refractive indexes of all fillers used in this investigation were measured in powder form before silanation by Fisher Scientific Wet Method. By this method, a small amount of powder is mixed with liquids of known refractive index. if the opacity of the mix is minimum, the refractive index of the liquid is equal to that of the liquid. The values given in Table IV below are with respect to Sodium line, 5893 Å at 25° C.

TABLE IV

Refractive indexes, 5893° A at 25° C.

| | Refractive indexes of liquid measured by Fisher Scientific Wet Method | Refractive indexes of reference liquids measured by Bausch & Lomb Refractometer |
|---|---|---|
| Fillers: | | |
| Lithium-Aluminum-Silicate | 1.520 ± .004 | 1.5197 |
| Boro-Barium- | | |

TABLE IV-continued

| | Refractive indexes, 5893° A at 25° C. | | | |
|---|---|---|---|---|
| Refractive indexes of liquid measured by Fisher Scientific Wet Method | | Refractive indexes of reference liquids measured by Bausch & Lomb Refractometer | | |
| Aluminum-Silicate | 1.540 ± .004 | 1.540 | | |
| Barium-Aluminum-Silicate | 1.576 ± .004 | 1.5742 | | |
| Fused Quartz | 1.460 ± .004 | 1.460 | | |
| Refractive index of BisGMA resin | | | | 1.5481 |
| | BisGMA resin (4.2 gm) | + 1,6 hexanediacrylate (.7 gm) | | 1.5340 |
| | BisGMA resin (4.2 gm) | + 1,6 hexanediacrylate (.7 gm) | + benzil (.02 gm) | 1.5340 |
| | BisGMA resin (4.2 gm) | + 1,6 hexanediacrylate (.7 gm) | + benzil (.2 gm) + trihexylamine (.05 gm) | 1.5322 |

In a strict sense the refractive indexes should be measured at the maximum output of irradiating light which is about 3,600 Å. The refractive indexes of the resin and the other ingedients (except filler) successively added to it in the same ratio as in composites were measured using Bausch & Lomb refractometer at 25° C. The values are included in Table III. The difference between two methods of estimation was checked by measuring the refractive index of reference liquids by the Bausch & Lomb method and the results agree very closely.

The fused quartz has the least matching refractive index with that of resin system and that is why the composite filled with quartz has the least strength. If the same reason extended to boro-barium-aluminum-silicate and barium-aluminum-silicate, the boro-barium-aluminum-silicate filled composite should have higher strength and higher UV penetration than barium-aluminum-silicate. Obviously, other factors such a composition or crystal structure are influencing the promotion of the UV transmittance to a higher level. Barium-aluminum-silicate absorbs almost completely the x-ray region of spectrum while it transmits a good portion of ultraviolet rays which fall on it in the resin system.

Other modifications and ramifications of the present invention would appear to those skilled in the art upon a reading of this disclosure. These are intended to be included within the scope of this invention.

What is claimed is:

1. A U.V. curable dental restorative composition which consists essentially of a blend of BisGMA resin and about 50 to 85 weight percent of an inorganic filler material which includes a barium-aluminum-silicate glass having the following composition in weight percent:

$SiO_2$: 25–40%
BaO: 35–55%
$Al_2O_3$: 15–30%.

2. A U.V. curable dental restorative composition which consists essentially of the following composition:

| | Parts by Weight |
|---|---|
| BisGMA | 10–20 |
| Diluent Monomer | 2–5 |
| Benzil | .001–1 |
| Trihexylamine | .01–1 |
| Barium Aluminum Silicate Filler | 70–85 | in which the composition of the filler material consists essentially of the following composition in weight percent:

$SiO_2$: 25–40%
BaO: 35–55%
$Al_2O_3$: 15–30%.

* * * * *